United States Patent [19]

Caprathe et al.

[11] Patent Number: 4,975,445

[45] Date of Patent: Dec. 4, 1990

[54] SUBSTITUTED CYCLOHEXENES AS CENTRAL NERVOUS SYSTEM AGENTS

[75] Inventors: Bradley W. Caprathe, Redford; Juan C. Jaen, Plymouth; Sarah J. Smith; Lawrence D. Wise, both of Ann Arbor, all of Mich.

[73] Assignee: Warner-Lambert Company, Morris Plains, N.J.

[21] Appl. No.: 446,950

[22] Filed: Dec. 6, 1989

[51] Int. Cl.$^5$ ............... A61K 31/495; A61K 31/435; A61K 31/445; C07D 401/14; C07D 403/04

[52] U.S. Cl. .................................... 514/252; 514/256; 514/318; 514/326; 514/333; 514/342; 544/295; 544/333; 544/357; 544/360; 544/364; 544/369; 544/379; 544/405; 546/193; 546/209; 546/212; 546/214; 546/216; 546/217; 546/268; 546/275; 546/280

[58] Field of Search ............... 544/295, 333, 357, 360, 544/364, 369, 379, 405; 546/193, 209, 212, 214, 216, 217, 268, 275, 280; 514/252, 256, 318, 326, 333, 342

[56] References Cited

U.S. PATENT DOCUMENTS 4,329,353  5/1982  Stokbroekx et al. ............... 546/199

FOREIGN PATENT DOCUMENTS 1311580  3/1973  United Kingdom .
1327691  8/1973  United Kingdom .

OTHER PUBLICATIONS

Carol A. Tamminga et al., Arch. Gen. Psychiatry, vol. 43, 1986, pp. 398–402.

Primary Examiner—Cecilia Shen
Attorney, Agent, or Firm—Francis J. Tinney

[57] ABSTRACT

Substituted cyclohexenes are described, as well as methods for the preparation and pharmaceutical composition of same, which are useful as central nervous system agents and are particularly useful as dopaminergic, antipsychotic, and antihypertensive agents as well as for treating hyperprolactinaemia-related conditions and central nervous system disorders.

6 Claims, No Drawings

SUBSTITUTED CYCLOHEXENES AS CENTRAL NERVOUS SYSTEM AGENTS

BACKGROUND OF THE INVENTION The present invention relates to novel substituted cyclohexenes useful as pharmaceutical agents, to methods for their production, to pharmaceutical compositions which include these compounds and a pharmaceutically acceptable carrier, and to pharmaceutical methods of treatment. The novel compounds of the present invention are central nervous system agents. More particularly, the novel compounds of the present invention are dopaminergic agents. A series of 1-(4-arylcyclohexyl)piperidines which may structurally be represented by the formula

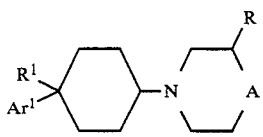

the pharmaceutically acceptable acid addition salts and the stereochemically isomeric forms thereof, wherein
$Ar^1$ is a member selected from the group consisting of aryl and 1,3-benzodioxolyl; R is a member selected from the group consisting of hydrogen and lower alkyl; $R_1$ is a member selected from the group consisting of hydrogen, cyano, carboxyl, lower alkyloxycarbonyl, aryllower alkyloxycarbonyl, aminocarbonyl, mono- and di(lower alkyl) aminocarbonyl, mono- and di(aryllower alkyl)aminocarbonyl, (aryllower alkyl)lower alkylamino carbonyl, hydroxy, lower alkyloxy, lower alkylcarbonyloxy, formyl, lower alkylcarbonyl, arylcarbonyl, aryllower alkylcarbonyl, lower alkyl, lower alkenyl, lower alkynyl and cyclohexyl; and
A is a bivalent radical, having the formula

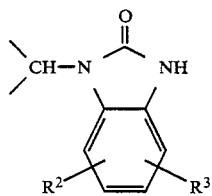

wherein
$R^2$ and $R^3$ are each independently selected from the group consisting of hydrogen, halo, trifluoromethyl, lower alkyl and lower alkyloxy; or
A is a bivalent radical having the formula

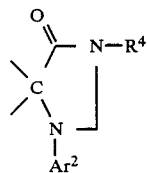

wherein
$Ar^2$ is aryl, and
$R^4$ is a member selected from the group consisting of hydrogen, lower alkyl, aryllower alkyl, cyanolower alkyl, aminolower alkyl, mono- and di(lower alkyl)aminolower alkyl, mono- and di(aryllower alkyl)aminolower alkyl, [(aryllower alkyl)lower alkylamino]lower alkyl, hydroxylower alkyl, mercaptolower alkyl, lower alkyloxylower alkyl, lower alkylthiolower alkyl, aryloxylower alkyl, arylthiolower alkyl, aryllower alkyloxylower alkyl, aryllower alkylthiolower alkyl, and a radical of formula

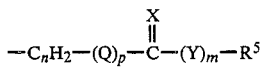

wherein
n is 0 or an integer from 1 to 6 inclusive, Q is O, S or $NR^6$, p is 0 or 1, X is O or S, $R^5$ is hydrogen, lower alkyl, aryl or aryllower alkyl, m is 0 or 1 and Y is O, S or $NR^6$, wherein $R^6$ as used in the definition of Q and Y is hydrogen, lower alkyl, aryl or aryllower alkyl;
provided that when Y is O and m and p are each 1 than $R^5$ is other than hydrogen and provided that when p is 1 than n is other than 0;
wherein aryl is a member selected from the group consisting of phenyl, thienyl, pyridinyl, naphthalenyl and substituted phenyl, said substituted phenyl having from 1 to 3 substituents each independently selected from the group consisting of halo, lower akyl, lower alkyloxy, phenyl lower alkyloxy, trifluoromethyl, nitro, amino and hydroxy are disclosed in U.S. Pat. No. 4,329,353 as having psychotropic and antiemetic activity.

A series of 4-phenylcyclohexenyamines represented by the formulae:

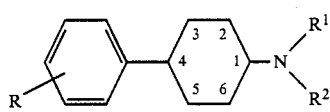

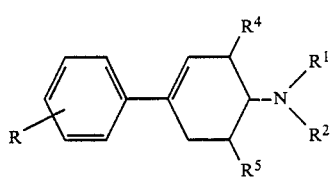

and

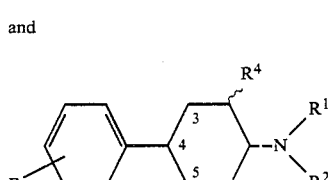

wherein R is hydrogen, methyl, ethyl, fluorine, chlorine, bromine, trifluoromethyl or alkoxy of from one to four carbon atoms; $R^1$ is hydrogen or alkyl of from one to four carbon atoms; $R^2$ is hydrogen, alkyl of from one to four carbon atoms, alkanoyl of from one to three carbon atoms, alkylsulfonyl of from one to three carbon atoms, arylsulfonyl of from six to ten carbon atoms, alkylcarbamonyl wherein alkyl is from one to four carbon atoms, alkoxycarbonyl wherein alkyl is from one to four carbon atoms, ring monosubstituted aroylalkyl wherein the substituents have the same meaning as R, above, aryl is from six to ten carbon atoms and alkyl is from one to six carbon atoms or bis(ring monosubstituted)arylalkyl wherein the substituents have the same meaning as R above, aryl is from six to ten carbon atoms and alkyl is from one to six carbon atoms or $R^1$ and $R^2$ taken together with

is a saturated heterocyclic amino radical selected from unsubstituted and monosubstituted (excluding halogen) pyrrolidino, piperidino and hexamethylenimino, in the compounds of Formula B, $R^1$ and $R^3$ are alkyl of from one to four carbon atoms; in the compounds of Formula C, $R^4$ is alkyl of from one to four carbon atoms, the 3(4)- and 4(5)-carbon atom linkages of the cyclohexane ring are either single bonds or double bonds, with the proviso that one of the two aforesaid linkages is a double bond and the other is a single bond, and ~ is a generic expression denoting cis and stereoconfiguration and mixtures thereof are disclosed in Great Britain Patent No. 1,327,691 as central nervous system depressants and blood pressure lowering agents.

A series of 4-(substituted phenyl) cyclohexylamine represented by the formula

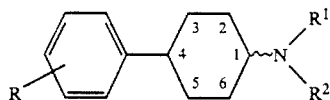

wherein ~ is a generic expression denoting cis and trans stereo configuration and mixtures thereof; R is alkyl of from one to four carbon atoms, fluorine, chlorine, bromine, trifluoromethyl or alkoxy of from one to four carbon atoms; $R^1$ is hydrogen or methyl; $R^2$ is hydrogen, methyl, alkoxy carbonyl wherein alkyl is from 1 to 2 carbon atoms, alkanoyl of from one to three carbon atoms, alkylsulfonyl of from one to three carbon atoms, arylsulfonyl of from six to ten carbon atoms, alkylcarbamoyl wherein alkyl is from one to four carbon atoms, alkoxycarbonyl wherein alkyl is from one to four carbon atoms, ring monosubstituted aroylalkyl wherein the substituents have the same meaning as R, above, aryl is from six to ten carbon atoms and alkyl is from one to six carbon atoms or bis (ring monosubstituted phenyl)alkyl wherein the substituents have the same meaning R, above, and alkyl is from one to six carbon atoms; or $R^1$ and $R^2$ when taken together with

is unsubstituted or monosubstituted (excluding halogen) pyrrolidino, piperidino or hexamethylenimino; and an acid addition salt thereof are disclosed in Great Britain Patent No. 1,311,580 as central nervous system agents.

However, the 1-(4-arylcyclohexyl) piperidines disclosed in U.S. Pat. No. 4,329,353, the 4-phenylcyclohexenylamines disclosed in Great Britain Patent No. 1,327,691 or the 4-(substituted phenyl)cyclohexylamines disclosed in Great Britain Patent No. 1,311,580 do not disclose or suggest the combination of structural variations of the compounds of the present invention described hereinafter.

SUMMARY OF THE INVENTION

Accordingly, the present invention is a compound

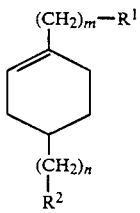

where $R^1$ is aryl, 2-, 3-, or 4-pyridinyl or 2-, 3-, or 4-pyridinyl substituted by lower alkyl, lower alkoxy, or halogen, 2-, 4-, or 5-pyrimidinyl or 2-, 4- or 5- pyrimidinyl substituted by lower alkyl, lower alkoxy, or halogen, 2-pyrazinyl or 2-pyrazinyl substituted by lower alkyl, lower alkoxy, or halogen, 2- or 3-thienyl or 2- or 3-thienyl substituted by lower alkyl or halogen, 2- or 3-furanyl or 2- or 3-furanyl substituted by lower alkyl or halogen, 2-, 4-, or 5-thiazolyl or 2-, 4- or 5-thiazolyl substituted by lower alkyl or halogen;

m is zero or an integer from one to two;

$R^2$ is

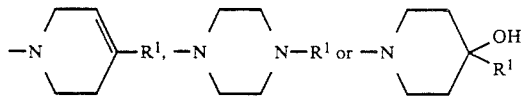

wherein $R^1$ is as defined above; n is zero or an integer from one to four; and corresponding optical isomers thereof; or a pharmaceutically acceptable acid additive salt thereof.

As dopaminergic agents, the compounds of Formula I are useful as antipsychotic agents for treating psychoses such as schizophrenia. They are also useful as antihypertensives and for the treatment of disorders which respond to dopaminergic activation. Thus, other embodiments of the present invention include the treatment, by a compound of Formula I, of hyperprolactinaemia-related conditions, such as galactorrhea, amenorrhea, menstrual disorders and sexual dysfunction, and several central nervous system disorders such as Parkinson's disease, Huntington's chorea, and depression. In addition, like many known antipsychotics, these compounds are high affinity ligands for the central nervous system sigma binding site.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "lower alkyl" means a straight or branched hydrocarbon radical having from one to six carbon atoms and includes, for example, methyl, ethyl, n-propyl, isopropyl, n-butyl, sec-butyl, isobutyl, tert-butyl, n-pentyl, n-hexyl, and the like.

The term "aryl" means an aromatic radical which is a phenyl group or phenyl group substituted by one to four substituents selected from lower alkyl, lower alkoxy, lower thioalkoxy, halogen or trifluoromethyl such as, for example, benzyl, phenethyl, and the like.

"Lower alkoxy" and "thioalkoxy" are O-alkyl or S-alkyl of from one to six carbon atoms as defined above for "lower alkyl."

"Halogen" is fluorine, chlorine, bromine, or iodine.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, magnesium, and the like.

Pharmaceutically acceptable acid addition salts of the compounds of Formula I include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, capryl-ate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al, "Pharmaceutical Salts," *Journal of Pharmaceutical Science,* Vol. 66, pages 1-19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the soluated forms; including hydrated forms, are equivalent to unsolvated forms and are intended to be encompassed within the scope of the present invention.

Certain of the compounds of the present invention possess asymmetric carbon atoms (optical centers); the racemates as well as the individual enantiomers are intended to be encompassed within the scope of the present invention.

A preferred compound of Formula I is one wherein R$^1$ is phenyl, phenyl substituted by para-lower alkyl, para lower alkoxy, para lower thioalkoxy, or para halogen, 2-, 3-, or 4-pyridinyl, 2-, or 3-furanyl, 2- or 3- thienyl, or 2-, 4-, or 5-thiazolyl; m is zero;

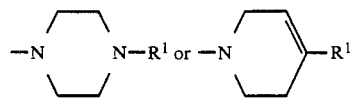

wherein R$^1$ is as defined above; and n is zero or an integer from one to three.

Another preferred embodiment is a compound of Formula I wherein
R$^1$ is phenyl, phenyl substituted by para-lower alkoxy, or para-halogen, 2-, 3-, or 4-pyridinyl, 2- or 3-thienyl, or 2-, 4-, or 5-thiazolyl;
m is zero;

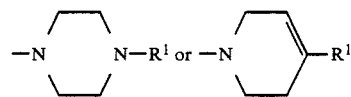

wherein R$^1$ is as defined above; and n is zero or an integer from one to two.

Particularly valuable are:
(±)-1-(2-Pyridinyl)5-[4-(2-pyridinyl)-3cyclohexen-1-yl]piperazine;
(±)-1(2-Pyridinyl)-4[4-(3-pyridinyl)-3-cyclohexen-1-yl]piperazine;
(±)-1-(2-Pyridinyl)-4-[4-(2-thienyl)-3-cyclohexen-1yl]-piperazine;
(±)-1-(2-Pyridinyl)-4-[4-(3-thienyl)-3-cyclohexen-1yl]-piperazine;
(±)-1-(4-Phenyl-3-cyclohexen-1-yl)-4-(2-pyridinyl)piperazine;
(±)-1-(2-Pyridinyl)-4-[[4-(2-thienyl)-3-cyclohexen1-yl]methyl]piperazine; (i)-1-(2-Pyridinyl)-4-[[4-(2-pyridinyl)-3-cyclohexen1-yl]methyl]piperazine;
(±)-1-(2-Pyridinyl)-4-[[4-phenyl-3-cyclohexen-1-yl]methyl]piperazine;
(±)-1-(2-Pyridinyl)-4-[2-[4-(2-thienyl)-3-cyclohexen-1yl]ethyl]piperazine;
(±)-1-[2-(4-Phenyl-3-cyclohexen-1-yl)ethyl]-4-(2-pyridinyl)piperazine;
(±)-1-(2-Pyridinyl)-4-[2-[4-(2-pyridinyl)-3-cyclohexen1-yl]ethyl]-piperazine;
(±)-1-[2-[4-(4-Fluorophenyl)-3-cyclohexen-1-yl]ethyl]4-(2-pyridinyl)piperazine;
(±)-1-(2-Pyridinyl)-4-[2-[4-(2-thiazolyl)-3-cyclohexen1-yl]-ethyl]piperazine;
(±)-1,2,3,6-Tetrahydro-4-phenyl-1-[2-[4-(2-thienyl)-3-cyclohexen-1-yl]-ethyl]pyridine; and
(±)-2-[4-(3,6-Dihydro-4-phenyl-1(2H)-pyridinyl)-1-cyclohexen-1-yl]pyridine; or a pharmaceutically acceptable acid addition salt thereof.

The compounds of Formula I are valuable dopaminergic agents. The tests employed indicate that compounds of Formula I possess dopaminergic activity. Thus, the compounds of Formula I were tested for their ability to inhibit locomotor activity in mice according to the assay described by J. R. McLean, et al, Pharmacoloqy, Biochemistry and Behavior, Volume 8, pages 97-99 (1978); for their ability to inhibit [$^3$H]-spiroperidol binding in a receptor assay described by D. Grigoriadis and P. Seeman, *Journal of Neurochemistry,* Volume 44, Pages 1925-1935 (1985); and for their ability to inhibit dopamine synthesis in rats according to the protocol described by J. R. Walters and R. H. Roth, *Naunyn-Schmiedeberg's Archives of Pharmacology*, Volume 296, pages 5–14 (1976). The above test methods are incorporated herein by reference. The data in the table show the dopaminergic activity of representative compounds of Formula I. Additionally, compounds of Formula I are ligands for the sigma opiate binding site. The data in the table show the inhibition of [$^3$H]DTG (ditoluoylguanidine, a sigma ligand) binding by representative compounds of Formula I, according to the method of E. Weber, et al. *Proceedings of the National Academy of Sciences*, USA, Volume 83, Pages 8784–8788 (1986).

nyl or 2- or 3-thienyl substituted by lower alkyl or halogen, 2- or 3-furanyl or 2- or 3-furanyl substituted by lower alkyl or halogen, 2-, 4-, or 5-thiazolyl or 2-, 4-, or 5-thiazolyl substituted by lower alkyl or halogen;

m is zero or an integer from one to two;

$R^2$ is

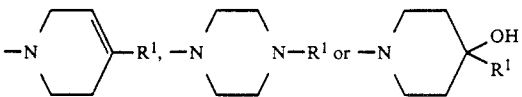

| | | Biological Activity of Compounds of Formula I | | | |
|---|---|---|---|---|---|
| Example Number | Compound | Inhibition of [$^3$H]-Spiroperidol Binding IC$_{50}$ nM | Inhibition of Locomotor Activity in Mice ED$_{50}$, ng/kg, IP | Effects on Brain Striatal Dopamine Synthesis in Rats at 10 mg/kg, IP | Inhibition of [$^3$H]DTG Binding IC$_{50}$ nM |
| 1a | (±)-1-(2-Pyridinyl)-4-[4-(2-pyridinyl)-3-cyclohexen-1-yl]-piperazine | 1180 | 0.9 | 75% inhibition | |
| 1 | (±)-1-(2-Pyridinyl)-4-[4-(3-pyridinyl)-3-cyclohexen-1-yl]-piperazine | 188 | 0.1 | 100% inhibition | |
| 2 | (±)-1-(2-Pyridinyl)-4-[4-(2-thienyl)-3-cyclohexen-1-yl]-piperazine | 352 | 9.3 | | |
| 2a | (±)-1-(4-Phenyl-3-cyclohexen-1-yl)-4-(2-pyridinyl)piperazine | 599 | 1.0 | | |
| 2b | (±)-1-(2-Pyridinyl)-4-[[4-(2-thienyl)-3-cyclohexen-1-yl]methyl]-piperazine | 2430 | <30 | | |
| 2c | (±)-1-(2-Pyridinyl)-4-[2-[4-(2-thienyl)-3-cyclohexen-1-yl]ethyl]-piperazine | | 8.4 | 46% inhibition | 39 |
| 2d | (±)-1-[2-(4-Phenyl-3-cyclohexen-1-yl)ethyl]-4-(2-pyridinyl)-piperazine | 409 | 1.9 | 48% inhibition | 23 |
| 1b | (±)-1-(2-Pyridinyl)-4-[2-[4-(2-pyridinyl)-3-cyclohexen-1-yl]-ethyl]piperazine | 128 | 0.4 | | 39 |
| 2e | (±)-1-[2-[4-(4-Fluorophenyl)-3-cyclohexen-1-yl]ethyl]-4-(2-pyridinyl)piperazine | 365 | 2.9 | 23% inhibition | 20 |
| 2f | (±)-1-(2-Pyridinyl)-4-[2-[4-(2-thiazolyl)-3-cyclohexen-1-yl]-ethyl]piperazine | 267 | 0.8 | 77% inhibition | 98 |
| 2g | (±)-1,2,3,6-Tetrahydro-4-phenyl-1-[2-[4-(2-thienyl)-3-cyclohexen-1-yl]ethyl]pyridine | 32 | 3.0 | | 2.0 |
| 3 | (±)-2-[4-(3,6-Dihydro-4-phenyl-1(2H)-pyridinyl)-1-cyclohexen-1-yl]-pyridine | 296 | 2.0 | | | compound of Formula 1

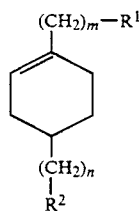

wherein
R$^1$ is aryl, 2-, 3-, or 4-pyridinyl or 2-, 3-, or 4-pyridinyl substituted by lower alkyl, lower alkoxy, or halogen, 2-, 4-, or 5- pyrimidinyl or 2-, 4-, or 5-pyrimidinyl substituted by lower alkyl, lower alkoxy, or halogen, 2-pyrazinyl or 2-pyrazinyl substituted by lower alkyl, lower alkoxy, or halogen, 2- or 3-thiewherein R$^1$ is as defined above; n is zero or an integer from one to four; and corresponding optical isomers thereof; or a pharmaceutically acceptable acid addition salt thereof, may be prepared by dehydrating a compound of Formula II.

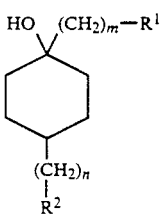

wherein $R^1$, m, $R^2$ and n are as defined above with a dehydrating reagent such as, for example, thionyl chloride, para-toluenesulfonic acid, methane sulfonic acid, sulfuric acid and the like optionally in the presence of a solvent such as for example benzene, toluene and the like, at about 0° C. to about 100° C. or if a solvent is employed to about the reflux temperature of the solvent for about 0.5 to about 24 hours to give a compound of Formula I A compound of Formula II is prepared by treating a compound of Formula III.

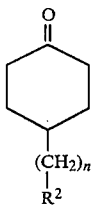
III wherein $R^2$ and n are as defined above with a compound of Formula IV $R^1$—$(CH_2)_m$—M    IV wherein M is magnesium-Hal, wherein Hal is halogen, or M is lithium and $R^1$ and m are as defined above, in the presence of a solvent such as, for example, tetrahydrofuran, diethyl ether, and the like at about −78° C. to about the reflux temperature of the solvent for about 0.5 to about 24 hours to give a compound of Formula II.

A compound of Formula III is prepared from a compound of Formula V

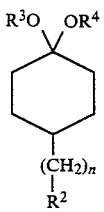
V wherein $R^3$ and $R^4$ are alkyl of one to six carbon atoms or $R^3$ and $R^4$ together are

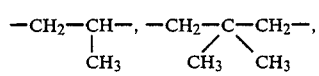

—$CH_2CH_2$— or —$CH_2CH_2CH_2$— and $R_2$ and n are as defined above by treatment with an acid such as, for example, a 10% aqueous solution of hydrochloric acid in the presence of a solvent such as, for example, acetone and the like to give a compound of Formula III.

A compound of Formula Va

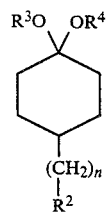
Va wherein n is zero and $R^2$, $R^3$ and $R^4$ are as defined above is prepared from a compound of Formula VI

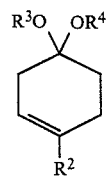
VI wherein $R^2$, $R^3$ and $R^4$ are as defined above by treatment with a reducing agent such as, for example, sodium cyanoborohydride and the like in a solvent such as, for example, methanol and the like in the presence of an acid such as, for example, hydrochloric acid and the like or alternatively reduction is carried out with hydrogen in the presence of a catalyst such as, for example, palladium on carbon in the presence of a solvent such as, for example, methanol and the like to give a compound of Formula Va.

A compound of Formula VI is prepared from a compound of Formula VII

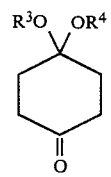
VII wherein $R^3$ and $R^4$ are as defined above by reaction with a compound of Formula VIII $R^2H$    VIII wherein $R^2$ is as defined above in the presence of a catalytic amount of an acid such as, for example, para-toluenesulfonic acid and the like in the presence of a solvent suited for the azeotropic removal of water such as, for example, toluene and the like to give a compound of Formula VI.

A compound of Formula V wherein n is an integer from 1 to 4 and $R^2$, $R^3$ and $R^4$ are as defined above is prepared from a compound of Formula IX

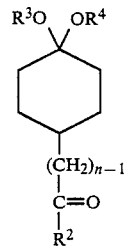
IX wherein n is an integer from 1 to 4 and $R^2$, $R^3$ and $R^4$ are as defined above by treatment with a reducing agent such as, for example, diborane, aluminum hydride and the like in a solvent such as, for example, tetrahydrofuran and the like to give a compound of Formula V.

A compound of Formula IX is prepared from a compound of Formula X.

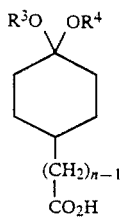

X wherein n is an integer from 1 to 4 and $R^3$ and $R^4$ are as defined above and a compound of Formula VIII. In order to obtain the reaction of these two compounds, a compound of Formula X must be activated in the presence of a chloroformate such as, for example, isobutyl chloroformate and a base such as, for example, triethylamine, or alternatively, a coupling reagent such as, for example, dicyclohexylcarbodiimide, carbonyldiimidazole and the like in the presence of a solvent such as, for example, dichloromethane and the like to give a compound of Formula IX.

A compound of Formula X is prepared from a compound of Formula XI

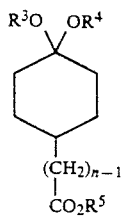

XI wherein n is an integer from 1 to 4, $R^5$ is lower alkyl and $R^3$ and $R^4$ are as defined above, by hydrolysis with a base such as, for example, potassium hydroxide and the like in an alcohol such as, for example, ethanol and the like to give a compound of Formula X.

A compound of Formula XI is prepared from a

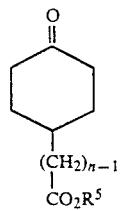

XII wherein n is an integer from 1 to 4 and $R^5$ is as defined above using conventional procedures known in the art.

Alternatively, a compound of Formula V is prepared from a compound of Formula XIII

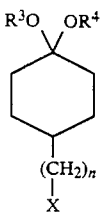

XIII wherein n is an integer from 1 to 4, X is halogen, $CH_3SO_2O-$, para—$CH_3C_6H_4SO_2O-$, and the like, and $R^3$, and $R^4$ are as defined above and a compound of Formula VIII in the presence of a base such as, for example, sodium bicarbonate and the like and a solvent such as, for example, dimethylformamide and the like to give a compound of Formula V.

A compound of Formula XIII is prepared from a compound of Formula XIV

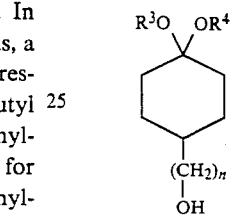

XIV wherein n is an integer from 1 to 4 and $R^2$ and $R^4$ are as defined above by treatment with thionyl chloride, thionyl bromide and the like in the presence of a solvent such as, for example, chloroform and the like or alternatively treatment with methanesulfonyl chloride, para-toluenesulfonyl chloride and the like in the presence of a base such as, for example, pyridine and the like to give a compound of Formula XIII.

A compound of Formula XIV is prepared from a compound of Formula XI wherein n is an integer from 1 to 4 and $R^3$, $R^4$ and $R^5$ are as defined above by treatment with a complex metal hydride such as, for example, diborane, lithium aluminum hydride and the like in the presence of a solvent such as, for example, tetrahydrofuran and the like to give a compound of Formula XIV.

Compounds of Formula IV, Formula VII, Formula VIII and Formula XII are either known or capable of being prepared by methods known in the art.

A compound of Formula I, which is a racemic mixture, may be further resolved into its enantiomers. Accordingly, as another aspect of the present invention, a compound of Formula (±)I may be resolved into its enantiomers by the use of conventional methodology such as, for example, optically active acids. Thus, the resulting diastereomeric salts may be separated by crystallization and then converted by conventional methodology to the optically active enantiomer (+)I or (−)I.

Additionally, compounds of Formula II which are used to prepare compounds of Formula I are valuable dopaminergic agents as well as potent ligands for the sigma opiate binding site. Thus a compound of Formula II would be useful in the treatment methods mentioned previously for a compound of Formula 1.

The compounds of the present invention can be prepared and administered in a wide variety of oral and parenteral dosage forms It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg preferably 10 mg to 100 mg according to the particular application and the potency of the active component. The composition can, if desired, also contain other compatible therapeutic agents.

In therapeutic use as antipsychotic agents, the compounds utilized in the pharmaceutical method of this invention are administered at the initial dosage of about 1 mg to about 50 mg per kilogram daily. A daily dose range of about 5 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1

($\pm$)-1-(2-Pyridinyl)-4-[4-(3-pyridinyl)-3-cyclohexen-1-yl]piperazine

A mixture of cis and trans-1-(3-pyridinyl)-4-[4-(2-pyridinyl)-1-piperazinyl]cyclohexanol (1.5 g) (Example A) is dissolved in 25 ml of 80% sulfuric acid. The mixture is heated at 60° C. for 6 hours. The solution is cooled in an ice bath, diluted with water and carefully neutralized with 50% sodium hydroxide. The product is isolated by extraction with dichloromethane, and purified by chromatography (silica gel; 2% methanol in dichloromethane) to give the title compound containing 0.25 molecules of water; mp 146–148° C.

In a process analogous to Example 1 using appropriate starting materials the corresponding compounds of Formula 1 are prepared as follows:

EXAMPLE 1a ($\pm$)-1-(2-Pyridinyl)-4-4-(2-pyridinyl)-3-cyclo-hexen-1-yl]piperazine, containing 0.2 molecules of water;

mp 186°–191° C.

EXAMPLE 1b ($\pm$)-1-(2-Pyridinyl)-4-[2-[4-(2-pyridinyl)-3-cyclohexen-1-yl]ethyl]piperazine, containing 0.2 molecules of water;

mp 108°–109° C.

EXAMPLE 2

($\pm$)-1-(2-Pyridinyl)-4-[4-(2-thienyl)-3-cyclohexen-1-yl]-piperazine

A solution of 2.0 g of a mixture of cis and trans-4-[4-(2-pyridinyl)-1-piperazinyl]-1-(2-thienyl)-cyclohexanol (Example $A_b$) is dissolved in 100 ml of benzene. About 1 ml of methanesulfonic acid is added, and the flask is fitted with a Dean-Stark trap for the removal of water. The reaction mixture is refluxed for about 4 hours. Following cooling to room temperature, 50 ml of sodium bicarbonate solution is added. The organic phase is further washed with brine, dried over magnesium sulfate and evaporated in-vacuo. The residue is purified by chromatography (silica gel; 2% methanol in dichloromethane) to afford the title compound containing 0.25 molecules of water; mp 156°-158° C.

In a process analogous to Example 2 using appropriate starting materials the corresponding compounds of Formula I are prepared as follows:

EXAMPLE 2a (±)-1-[(4-Phenyl)-3-cyclohexen-1-yl]-4-(2-pyridinyl)-piperazine, containing 0.1 molecules of water;

mp 169°-172° C.

EXAMPLE 2b (±)-1-(2-Pyridinyl)-4-[4-(2-thienyl)-3-cyclohexen-1-yl]methyl]piperazine, dihydrochloride, hemihydrate;

mp 265° C.

EXAMPLE 2c (±)-1-(2-Pyridinyl)-4-[2-[4-(2-thienyl)-3-cyclo-hexen-1-yl]ethyl]piperazine;

mp 117°-120° C.

EXAMPLE 2d (±)-1-[2-(4-Phenyl-3-cyclohexen-1-yl)ethyl -4-(2-pyridinyl)piperazIne, containing 0.2 molecules of water;

mp 115°-116° C.

EXAMPLE 2e (±)-1-[2-[4-(4-Fluorophenyl)-3-cyclohexen-1-yl]ethyl]-4-(2-pyridinyl)piperazine;

mp 133°-137° C.

EXAMPLE 2f (±)-1-(2-Pyridinyl)-4-[2-4-(2-thiazolyl)-3-cyclohexen-1-yl]ethyl]piperazine;

mp 109°-111° C.

EXAMPLE 2g (±)-1,2,3,6-Tetrahydro-4-phenyl-1-[2-4-(2-thienyl)-3-cyclohexen-1-yl]ethyl]piperazine containing 0.25 molecules of water; mp 114°-117° C.

EXAMPLE 3

(±)-2-[4-(3,6-Dihydro-4-phenyl-1(2H)-pyridinyl)-1-cyclohexen-1-yl]pyridine

A solution of 2.88 g of a mixture of cis- and trans-4-(3,6-dihydro-4-phenyl-1(2H)-pyridinyl)-1(2-pyridinyl)-cyclohexanol (Example A$_k$) in 144 ml of thionyl chloride is refluxed for 4 hours. The mixture is cooled in an ice bath and carefully diluted with water. The solution is made basic with ammonium hydroxide, extracted with dichloromethane, dried over sodium sulfate and evaporated in-vacuo. The residue is purified by chromatography (silica gel; 2.5% methanol in dichloromethane), to afford the title compound containing 1.5 molecules of water; mp 142.8-143.7° C.

PREPARATION OF STARTING MATERIALS

EXAMPLE A 1-(3-Pyridinyl)-4-[4-(2-pyridinyl)-1-piperazinyl]cyclohexanol (mixture of cis/trans)

STEP A: Preparation of 4-[4-(2-Pyridinyl)-1-piperazinyl]cyclohexanone.

A solution of 1,4-cyclohexanedione monoethyleneketal (50.0 g), 1-(2-pyridyl)piperazine (52.16 g), and p-toluenesulfonic acid (0.5 g) in 500 ml of toluene is refluxed with a Dean-Stark trap until the theoretical amount of water is collected (about four hours). The solvent is evaporated in vacuo and the residue is dissolved in 750 ml of methanol. This solution is cooled in an ice bath and sodium cyanoborohydride (30.1 g) is added in small portions over a two-minute period. The resulting suspension is stirred mechanically and over the next 30 minutes enough concentrated hydrochloric acid solution is added dropwise to the reaction mixture to maintain a pH of about 4. The solvent is removed in vacuo to leave a semisolid residue which is dissolved in 300 ml of a 10% solution of hydrochloric acid in a well ventilated fume hood. This solution is diluted with an equal volume of acetone and refluxed for two hours. The volatile components of the mixture are removed in vacuo and the residue is cooled in an ice bath and made basic with concentrated ammonium hydroxide. The white solid which forms is recrystallized from ethyl acetate-heptane to give 52.4 g of the title compound; mp 142°-144° C.

Step B: Preparation of 1-(3-Pyridinyl)-4-[4-(2-pyridinyl)-1-piperazinyl]cyclohexanol (mixture of cis/trans)

A solution of 4.74 g (30 mmol) of 3-bromopyridine in 100 ml of diethyl ether is cooled to −78° C. under a nitrogen atmosphere. n-Butyllithium (18.75 ml, 30 mmol) is added dropwise. The resulting suspension is stirred for 30 minutes. To this solution is added a solution of 5.19 g of 4-[4-(2-pyridinyl)-1-piperazinyl]cyclohexanone in 175 ml of tetrahydrofuran dropwise. The cold bath is removed and the mixture is allowed to warm to room temperature and quenched with 50 ml of saturated ammonium chloride solution. The tetrahydrofuran is evaporated under vacuum and the residue is partitioned into water/dichloromethane. The organic phase is separated and dried over magnesium sulfate and evaporated in vacuo to give the title compound as a mixture of cis and trans isomers.

The isomers are separated by chromatography on silica gel using 3% methanol:97% dichloromethane as eluant.

trans-1-(3-Pyridinyl)-4-[4-(2-pyridinyl)-1-piperazinyl]-cyclohexanol; mp 153°-158° C;

cis-1-(3-Pyridinyl)-4-[4-(2-pyridinyl)-1-piperazinyl]cyclohexanol; mp 175°-179° C.

In a process analogous to Example A using appropriate starting materials the following compounds are prepared

EXAMPLE A$_a$ cis-1-(2-Pyridinyl)-4-[4-(2-pyridinyl)-1-piperazinyl]-cyclohexanol;

mp 130°-134° C.

trans-1-(2-Pyridinyl)-4-[4-(2-pyridinyl)-1-piperazinyl]-cyclohexanol;

mp 86°-93° C.

EXAMPLE A_b 4-(2-Pyridinyl)-1-piperazinyl]-1-(2-thienyl)cyclohexanol (mixture of cis/trans);

mp 130°-135° C.

EXAMPLE A_c

1-Phenyl-4-[4-(2-pyridinyl)-1-piperazinyl]cyclohexanol (mixture of cis/trans);

mp 164°-172° C.

EXAMPLE A_d trans-4-[[4-(2-Pyridinyl)-1-piperazinyl]methyl]-1-(2-thienyl)cyclohexanol;

mp 50°-52° C;

cis-4-[[40(2-Pyridinyl)-1-piperazinyl]methyl]-1-(2-thienyl)cyclohexanol;

mp 114-117° C.

EXAMPLE A_e

4-[2-[4-(2-Pyridinyl)-1-piperazinyl]ethyl]-1-(2-thienyl)cyclohexanol (mixture of cis/trans);

mp 124°-140° C.

cis-4-[2-[4-(2-Pyridinyl)-1-piperazinyl]ethyl]-1-(2-thienyl)cyclohexanol;

mp 151°-154° C.

trans)-4-[2-[4-(2-Pyridinyl)-1-piperazinyl]ethyl]-1-(2-thienyl)cyclohexanol;

mp 108°-109° C.

EXAMPLE A_f

1-Phenyl-4-[2-[4-(2-pyridinyl)-1-piperazinyl[ethyl[-cyclohexanol (mixture of cis/trans);

mp 158°-163° C.

EXAMPLE A_g 1-(2-Pyridinyl)-4-[2-[4-(2-pyridinyl)-1-piperazinyl]-ethyl]cyclohexanol (mixture of cis/trans);

mp 100°-105° C.

EXAMPLE A_h 1-(4-Fluorophenyl)-4-[2-[4-(2-pyridinyl)-1-piperazinyl]ethyl]cyclohexanol (mixture of cis/trans);

mp 172°-177° C.

EXAMPLE A_i

4-[2-[4-(2-Pyridinyl)-1-piperazinyl]ethyl]-1-(2-thiazolyl)cyclohexanol (mixture of cis/trans);

mp 65°-80° C.

EXAMPLE A_j cis-4-[2-(3,6-Dihydro-4-phenyl-1(2H)-pyridinyl)ethyl]-1-(2-thienyl)cyclohexanol;

mp 164°-170° C.

EXAMPLE A_k 4-(3,6-Dihydro-4-phenyl-1(2H)-pyridinyl)-1-(2-pyridinyl)cyclohexanol (mixture of cis/trans);

mp 157°-159° C.

We claim:

1. A compound of Formula I

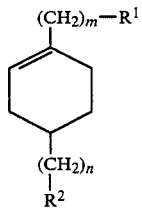

wherein p1 $R^1$ is phenyl, phenyl substituted by one to four substituents selected from the group consisting of lower alkyl, lower alkoxy, lower thioalkoxy, halogen, and trifluoromethyl, 2-, 30, or 4-pyridinyl or 2-, 3-, or 4-pyridinyl substituted by lower alkyl, lower alkoxy, or halogen, 2-, 4-, or 5-pyrimidinyl or 2-, 4-, or 5-pyrimidinyl substituted by lower alkyl, lower alkoxy, or halogen, 2-pyrazinyl or 2-pyrazinyl substituted by lower alkyl, lower alkoxy, or halogen, 2- or 3-thienyl or 2- or 3-thienyl substituted by lower alkyl or halogen, 2- or 3-furanyl or 2- or 3-furanyl substituted by lower alkyl or halogen, 2-, 4-, or 5-thiazolyl or 2-, 4-, or 5-thiazolyl substituted by lower alkyl or halogen;

m is zero or an integer from one to two;

$R^2$ is

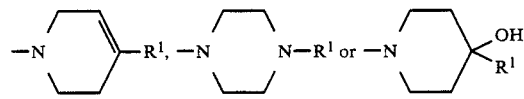

wherein $R^1$ is as defined above;

n is zero or an integer from one to four; and corresponding optical isomers thereof; or a pharmaceutically acceptable acid addition salt thereof.

2. A compound according to claim 1, in which $R^1$ is phenyl, phenyl substituted by para-lower alkyl, para lower alkoxy, para lower thioalkoxy, or para halogen, 2-, 3-, or 4-pyridinyl, 2-, or 3-furanyl, 2- or 3-thienyl, or 2-, 4-, or 5-thiazolyl;

m is zero;

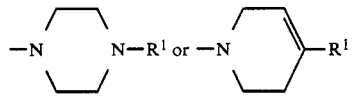

wherein $R^1$ is as defined above; and n is zero or an integer from one to three.

3. A compound according to claim 2, in which $R^1$ is phenyl, phenyl substituted by para-lower alkoxy or para-halogen, 2-, 3-, or 4-pyridinyl, 2or 3-thienyl, or 2-, 4-, or 5-thiazolyl;

m is zero;

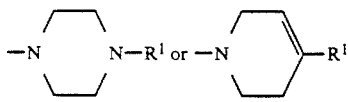

wherein R¹ is as defined above; and n is zero or an integer from one to two.

4. A compound according to claim 3 selected from the group consisting of:

(±)-(2-Pyridinyl)-4-[4-(2-pyridinyl)-3-cyclohexen-1-yl]piperazine;

(±)-1-(2-Pyridinyl)-4-[4-(3-pyridinyl)-3-cyclohexen-1-yl]piperazine;

(±)-1-(2-Pyridinyl)-4-[4-(2-thienyl)-3-cyclohexen-1-yl]piperazine;

(±)-1-(2-Pyridinyl)-4-[4-(3-thienyl)-3-cyclohexen-1-yl]piperazine;

(±)-1-(4-Phenyl-3-cyclohexen-1-yl)-4-(2-pyridinyl)piperazine;

(±)-1-(2-Pyridinyl)-4-[4-(2-thienyl)-3-cyclohexen-1-yl]methyl]piperazine;

(±)-1-(2-Pyridinyl)-4-[[4-(2-pyridinyl)-3-cyclohexen-1-yl]methyl]piperazine;

(±)-1-(2-Pyridinyl)-4-[4-phenyl-3-cyclohexen1-yl]methyl]piperazine;

(±)-1-(2-Pyridinyl)-4-[2-[4-(2-thienyl)-3-cyclohexen-1-yl]ethyl]piperazine;

(±)-1-[2-(4-Phenyl-3-cyclohexen-1-yl)ethyl]-4-(2-pyridinyl)piperazine;

(±)-1-(2-Pyridinyl)-4-[2-[4-(2-pyridinyl)-3-cyclohexen-1-yl]ethyl]piperazine;

(±)-1-[2-[4-(4-Fluorophenyl)-3-cyclohexen-1-yl]-ethyl]-4-(2-pyridinyl)piperazine;

(±)-1-(2-Pyridinyl)-4-[2-[4-(2-thiazolyl)-3-cyclohexen-1-yl]ethyl]piperazine;

(±)-1,2,3,6-Tetrahydro-4-phenyl-1-[2-[4-(2-thienyl)3-cyclohexen-1-yl]-ethyl]pyridine; and (±)-2-[4-(3,6-Dihydro-4-phenyl-1(2H)-pyridinyl)-1-cyclohexen-1-yl]pyridine.

5. A method of treating schizophrenia comprising administering to a host suffering therefrom a therapeutic effective amount of a compound according to claim 1 in unit dosage form.

6. A pharmaceutical composition adapted for administration as a dopaminergic, antipsychotic, antihypertensive or antidepressant agent comprising a therapeutic effective amount of a compound according to claim 1 in admixture with a pharmaceutically acceptable excipient, diluent or carrier.

* * * * *

UNITED STATES PATENT AND TRADEMARK OFFICE
CERTIFICATE OF CORRECTION

PATENT NO. : 4,975,445
DATED : December 4, 1990
INVENTOR(S) : Bradley W. Caprathe, et al It is certified that error appears in the above—identified patent and that said Letters Patent is hereby corrected as shown below:

In column 18,
    line 20, claim 1, delete "pl";
    line 23, claim 1, delete "30" and insert --3--;
    line 56, claim 2, insert --$R^2$ is-- before first structure.

In column 19,
    line 1, claim 3, insert --$R^2$ is-- before first structure;
    line 12, claim 4, in the first compound, after
        "(±)-" insert -- 1- --.

Signed and Sealed this

Thirty-first Day of March, 1992

Attest:

HARRY F. MANBECK, JR.

*Attesting Officer*      *Commissioner of Patents and Trademarks*